US009065055B2

(12) United States Patent
Zeika et al.

(10) Patent No.: US 9,065,055 B2
(45) Date of Patent: Jun. 23, 2015

(54) METHOD FOR PREPARING DOPED ORGANIC SEMICONDUCTOR MATERIALS AND FORMULATION UTILIZED THEREIN

(75) Inventors: Olaf Zeika, Dresden (DE); Andrea Lux, Dresden (DE); Andre Gruessing, Mannheim (DE); Michael Limmert, Dresden (DE); Horst Hartmann, Dresden (DE); Ansgar Werner, Dresden (DE); Martin Ammann, Dresden (DE)

(73) Assignee: NOVALED AG, Dresden (DE)

( * ) Notice: Subject to any disclaimer, the term of this patent is extended or adjusted under 35 U.S.C. 154(b) by 812 days.

(21) Appl. No.: 12/293,765

(22) PCT Filed: Mar. 21, 2007

(86) PCT No.: PCT/EP2007/002510
§ 371 (c)(1),
(2), (4) Date: Jan. 27, 2009

(87) PCT Pub. No.: WO2007/107356
PCT Pub. Date: Sep. 27, 2007

(65) Prior Publication Data
US 2010/0233844 A1    Sep. 16, 2010

(30) Foreign Application Priority Data

Mar. 21, 2006  (EP) ..................................... 06005687
Mar. 22, 2006  (EP) ..................................... 06005834

(51) Int. Cl.
C30B 30/00    (2006.01)
H01L 31/04    (2014.01)
H01L 51/00    (2006.01)
C07D 285/10   (2006.01)
C07D 271/107  (2006.01)
C09K 11/06    (2006.01)
H05B 33/14    (2006.01)
H05B 33/20    (2006.01)
H01L 51/50    (2006.01)

(52) U.S. Cl.
CPC ............ *H01L 51/002* (2013.01); *C07D 285/10* (2013.01); *H01L 51/0062* (2013.01); *H01L 51/5052* (2013.01); *C07D 271/107* (2013.01); *C09K 11/06* (2013.01); *C09K 2211/1011* (2013.01); *C09K 2211/1029* (2013.01); *C09K 2211/1088* (2013.01); *H01L 51/0053* (2013.01); *H01L 51/0054* (2013.01); *H01L 51/0067* (2013.01); *H01L 51/007* (2013.01); *H01L 51/0081* (2013.01); *H05B 33/14* (2013.01); *H05B 33/20* (2013.01); *Y02E 10/549* (2013.01)

(58) Field of Classification Search
CPC .................................................. H01L 51/002
USPC ................. 252/500–511; 423/445 R; 257/40; 528/423; 438/99
See application file for complete search history.

(56) References Cited

U.S. PATENT DOCUMENTS

| 3,644,770 | A | 2/1972 | Bell |
| 3,673,011 | A | 6/1972 | Strull |
| 3,913,999 | A | 10/1975 | Clarke |
| 5,093,698 | A | 3/1992 | Egusa |
| 5,198,153 | A | 3/1993 | Angelopoulos et al. |
| 5,315,129 | A | 5/1994 | Forrest et al. |
| 5,922,396 | A | 7/1999 | Thompson et al. |
| 6,287,712 | B1 | 9/2001 | Bulovic et al. |
| 6,312,836 | B1 | 11/2001 | Bulovic et al. |
| 6,376,655 | B1 * | 4/2002 | Berg et al. ..................... 534/573 |
| 6,387,546 | B1 | 5/2002 | Hamada et al. |
| 6,605,317 | B1 | 8/2003 | Kathirgamanathan et al. |
| 6,620,528 | B1 | 9/2003 | Yamazaki |
| 6,746,770 | B1 * | 6/2004 | Afzali-Ardakani et al. ................... 428/411.1 |
| 6,809,333 | B2 | 10/2004 | Ishikawa et al. |
| 6,818,329 | B1 | 11/2004 | Liao et al. |
| 2001/0055841 | A1 | 12/2001 | Yamazaki et al. |
| 2002/0009650 | A1 * | 1/2002 | Michot et al. .................. 429/314 |
| 2003/0180457 | A1 | 9/2003 | Murakami et al. |
| 2003/0197465 | A1 | 10/2003 | Qui et al. |
| 2004/0016907 | A1 | 1/2004 | Shi |
| 2004/0037987 | A1 | 2/2004 | Carlton et al. |
| 2004/0173929 | A1 | 9/2004 | Ghosh et al. |

(Continued)

FOREIGN PATENT DOCUMENTS

| DE | 10261609 | 7/2004 | |
| DE | WO2005086251 A2 * | 3/2005 | ............. H01L 51/00 |
| JP | 5931865 | 2/1984 | |
| JP | 7-196780 A | 8/1995 | |
| JP | 2001-319698 A | 11/2001 | |
| JP | 2005/167175 | 6/2005 | |
| JP | 2005/525696 | 8/2005 | |
| KR | 10-2004-0028954 A | 11/2005 | |
| KR | 10-2005-0107238 A | 5/2006 | |
| WO | 2002/093664 | 11/2002 | |
| WO | WO03/088271 | 10/2003 | |
| WO | 2004/070787 | 8/2004 | |

OTHER PUBLICATIONS

Wheland et al. ("Synthesis of Electrically Conductive Organic Solids." JACS, 98(13), pp. 3916-3925, Jun. 23, 1976).*

(Continued)

*Primary Examiner* — Tri V Nguyen
(74) *Attorney, Agent, or Firm* — Sutherland Asbill & Brennan LLP

(57) ABSTRACT

The present invention relates to a method for preparing doped organic semiconductor materials as well as a formulation which may be utilized in that method. The doped organic semiconductor materials are prepared by preparing a solution or suspension containing at least one dopant precursor, at least one organic material to be doped, and a solvent. The solution or suspension is then applied onto a substrate. After removing the solvent, the dopant precursor is converted into a dopant by application of activation energy. The dopant precursor, which is a dimer, oligomer, polymer, dispiro compound, or polycycle, is cleaved by the application of activation energy.

13 Claims, No Drawings

(56) References Cited

U.S. PATENT DOCUMENTS

| | | | |
|---|---|---|---|
| 2004/0220332 A1* | 11/2004 | Ho et al. .................. | 525/50 |
| 2005/0016461 A1 | 1/2005 | Klug et al. | |
| 2005/0023974 A1 | 2/2005 | Chwang et al. | |
| 2005/0040390 A1 | 2/2005 | Pfeiffer et al. | |
| 2005/0042548 A1 | 2/2005 | Klauk et al. | |
| 2005/0061232 A1 | 3/2005 | Werner et al. | |
| 2005/0072971 A1 | 4/2005 | Marrocco et al. | |
| 2005/0136232 A1 | 6/2005 | Forrest et al. | |
| 2005/0145179 A1 | 7/2005 | Cattaneo | |
| 2005/0179370 A1 | 8/2005 | Nakayama et al. | |
| 2006/0079004 A1 | 4/2006 | Werner et al. | |
| 2007/0249148 A1 | 10/2007 | Werner et al. | |
| 2007/0278479 A1 | 12/2007 | Werner et al. | |
| 2009/0011582 A1 | 1/2009 | Birnstock et al. | |
| 2009/0179189 A1 | 7/2009 | Werner et al. | |

OTHER PUBLICATIONS

Giffard et al. ("The First Evidence for the Generation of Radicals and Formation of Electrically Conducting Molecular Materials by Protic Doping of Tetrathiafulvalenes." Adv Mater, 6(4), pp. 298-300, 1994).*

Baldo, M. A., et al., "Low pressure vapor phase deposition of small molecular weight organic light emitting device structures," Appl. Phys. Lett., 71 (21), Nov. 24, 1997, p. 3033.

Baldo, M., et al., "Organic vapor phase deposition," Advanced Materials, 1998, 10, No. 18, pp. 1505-1514.

Bard, A. J., Faulkner, R.J., Electrochemical Methods: Fundamentals and Applications, Wiley, 2nd Ed., 2000.

Bloom, C. J. et al., "Low work function reduced metal complexes as cathodes in organic electroluminescent devices," J. of Phyiscal Chemistry B, vol. 107, No. 13, pp. 2933-2938.

Burrows, P.E. et al., "Organic vapor phase deposition: a new method for the growth of organic thin films with large optical non-linearities," Journal of Crystal Growth, 156, 1995, pp. 91-98.

Elwell, D., "Electrocrystallization of semiconducting materials from molten salt and orgnaic solutions," Journal of Crystal Growth, vol. 52, 1981, pp. 741-752.

Gao Y. et al., "Cs doping and energy level shift in CuPC", Chemical Physics Letters. North-Holland, Amsterdam, NL, vol. 380, Oct. 21, 2003, p. 451-455.

Gebeyehu, et al., "Bulk-heterojunction photovoltaic devices based on donor-acceptor organic small molecules blends," Solar Energy Materials and Solar Cells, 2003, vol. 79, pp. 81-92 (p. 1-11).

Harada, Kentaro et al., "Realization of organic pn-homojunction using a novel n-type doping technique, Proceedings of SPIE—The international Society for Optical Engineering; Organic Optoelectronics and Photonics 2004," vol. 5464, Sep. 2004, pp. 1-9.

Jianmin Shi, et al., "Doped Organic Electroluminescent Devices with Improved Stability," Appl. Phys. Lett. 70(13), Mar. 31, 1997, pp. 1665-1667.

Muramatsu, T. et al., "Preparation and Properties of a novel heterocyclic dispiro compound, 3, 10-diaza-N,N-dimethyldispiro[5.0.5.3]pentadeca-1,4,8,11-tetraene," Chemistry Letters, pp. 151-152, (1996).

Pfeiffer, M, et al., "Doped Organic semiconductors: physics and application in light emitting diodes," Organic Electronics, Elsevier, Amsterdam, NL, vol. 4, No. 2/3, Sep. 2003, pp. 89-103, XP001177135, ISSN: 1556-1199.

Shtein, Max et al., "Effects of film morphology and gate dielectric surface preparation on the electrical characteristics of organic-vapor-phase-deposited pentacene thin-film transistors," Applied Physics Letters, vol. 81, No. 2, p. 268, Jul. 8, 2002.

Shtein, Max et al., "Material transport regimes and mechanisms for growth of molecular organic thin films using low-pressure organic vaprot phase deposition," Journal of Applied Physics, vol. 89, No. 2, p. 1470, Jan. 15, 2001.

Tang, C. W., et al., "Electroluminescence of doped organic thin films," Journal of Applied Physics, (1989), vol. 65:9, pp. 3610-3616.

Tang, C.W. et al., "Organic electroluminescent diodes," Applied Physics Letters, vol. 51, No. 12, Sep. 21, 1987, pp. 913-915.

Tsiper, E.V. and Soos, Z.G.; "Charge redistribution and polarization energy of organic molecular crystals," Physical Review B; vol. 64; 195124-1.

Vaid T.P. et al, "Investigations of the 9,10-diphenylacridyl radical as an isostructural dopant for the molecular semiconductor 9, 10-diphenylanthracene," Chemistry of Materials, American Chemical Society, Bd. 15, Nr. 22, 4292-4299 (2003).

Wintgens, V. et al., "Reduction of Pyrylium Salts: Study by ESR and UV_Visible Spectroscopy of the Reversible Dimerization of the Pyranyl Radical," New. J. Chem., 10/6, 345-350 (1986).

Zhou C. et al., "Modulated chemical doping of individual carbon nanotubes," Science, American Association for the Advancement of Science, vol. 290, No. 5496, pp. 1552-1555.

Zhou, Theodore X, et al., "Stable and efficient electrophosphorescent organic light-emitting devices grown by organic vapor phase deposition," Applied Physics Letters, 86, 021107 (2005).

Response to Office Action; U.S. Appl. No. 11/576,553; (Sep. 25, 2009).

Non-Final Office Action; U.S. Appl. No. 11/576,553; (Jun. 25, 2009).

Non-final Rejection; U.S. Appl. No. 11/241,477; Jun. 18, 2007.

Response to Office Action; U.S. Appl. No. 11/241,477; Sep. 18, 2007.

Non-final Rejection; U.S. Appl. No. 11/241,477; Dec. 14, 2007.

Notice of Allowance; U.S. Appl. No. 11/241,477; Jun. 13, 2008.

Non-final Office Action, U.S. Appl. No. 10/595,319; Jan. 11, 2010.

Hamm, S. "Rectifying organic juntions of molecular assemblies based on perylene ion salts," J. Chem. Phys., vol. 103, No. 24, Dec. 22, 1995, pp. 10689-10695.

Blochwitz, J. et al., "Interface electronic structure of organic semiconductors with controlled doping levels," Org. Electronics 2, 97 (2001).

Akers, K.L. et al., "The Spatially Resolved Composition of K-Doped C60 Films," Thin Solid Films, vol. 257 (1995): pp. 204-210.

Yamashita, K. et al., "Fabrication of an Organic p-n Homojunction Diode Using Electrochemically Cation- and Photochemically Anion-Doped Polymer," Jpn. J. Appl. Phys., vol. 34 (Jul. 1995); pp. 3794-3797.

Werner, A.G. et al., "n-Type Doping of Organic Thin Films Using Cationic Dyes," Adv. Funct. Mater., vol. 14, No. 3 (Mar. 2004): pp. 255-260.

Werner, A. G. et al., "Pyronin B as a donor for n-type doping of organic thin films," Applied Physics Letters, vol. 82, No. 25, Jun. 23, 2003, pp. 4495-4497.

Nollau, A. et al., "Controlled n-type doping of a molecular organic semiconductor: naphthalenetetracarboxylic dianhydride (NTCDA) doped with bis(ethylenedithio)-tetrathiafulvalene (BEDT-TTF)," J. Appl. Phys., vol. 87, No. 9, May 1, 2006, pp. 4340-4343.

Disclosure Under 37 C.F.R. 1.56 U.S. Appl. No. 12/293,765 (Submitted herewith).

Ludvik, J. and Pragst, F. et al., "Electrochemical generation of triplet states," Journal of Electroanalytical Chemistry, No. 180, pp. 141-156, (1984).

Akiba, Kin-Ya et al., "Direct Synthesis of 2,2-diaryl-3-methyl-2,3-dihydrobenzothiazoles from 3-methyl-2,3-dihydrobenzothiazole-2-thione and some mechanistic aspects," Bulletin of the Chemical Society of Japan, vol. 52(1), pp. 156-159, (1979).

A. R. Siedle and R. B. Johannesen, "Reduction of the 1,3-dithiolium cation with hexacarbonylvanadate" Journal of Organic Chemistry Bd. 4-, NR. 13 1975, Seite 2202, XP002396000, Verbindungen 1 und 2, Seite 2202.

H. Jadamus, Q. Fernando and H. Freiser, "metal-ion induced rearrangements of bisbenzthiazolines to Schiff-base chelates", Journal of the American Chemical Society, Bd. 86, 1964, Seiten 3056-3059, XP002396001, Verbindung II, Seite 3056. Verbindungen Va-c, Seite 3058.

E. J. Corey, F. A. Carey and R. .A Winter: 1,2,4 "Stereospecific syntheses of olefins from 1, 2-thionocarbonates and 1,2-thrithiocarbonates, Trans-cycloheptene" Journal of the American Chemical Society, Bd. 87, Nr. 4, 1965, Seiten 934-935, XP002396002, Verbindung V, Seite 935.

(56) References Cited

OTHER PUBLICATIONS

E. Bayer and E. Breitmaier, "Die reaktion 1, 2, 4 von Benzil mit 2-Aminothiopheno I" Tetrahedron Letters, Bd. 15 1966, Seiten 1689-1693, XP002396003, Verbindung II, Seite 1689.

H. G. Mautner, "Potential deoxyribonucleic acid cross-linking agents. 8,8'-bispurines", Journal of Organic Chemistry Bd. 26, 1961, Seiten 1914-1917, XP002396004 Verbindung I, Seite 1915.

R. C. Elderfield and E. C. McClenachan, "Pyrolisis of the products of the reaction of o-aminobenzenethiols with ketones", Journal of the American Chemical Society, Bd. 82, 1960, Seiten 1982-1988, XP002396005, Verbindung VII, Seite 1983.

M. G. Miles, J. S. Wager and J. D. Wilson: 1, 2, 7, "Reactions of 4,5-dicyano-1,3-dithiole-2-thione and 1,3-dithiol-2-one with tervalent phosphorous compounds", Journal of Organic Chemistry, Bd. 40, Nr, 18, 1975, Seiten 2577-2582, XP002396006, Verbindung 5, Scheme II, Seite 2579.

Disclosure Under 37 C.F.R. Section 1.56 for U.S. Appl. No. 12/293,765 submitted herewith.

Long, M., "41.4: New Capabilities in Vacuum Thermal Evaporation Sources for Small Molecule OLED Manufacturing", SID 06 Digest, pp. 1474-1476, 2006.

Japanese Office Action which issued in Japanese counter part Application No. 2007-075684 (English Translation)(Jul. 27, 2010).

Parsons, R. "Manual of Symbols and Terminology for Physicochemical Quantities and Units, Appendix III, Electrochemical Nomenclature," International Union of Pure and Applied Chemistry—Division of Physical Chemistry, London Butterworths, 1973.

Gritzner G. and Kuta, J. "Recommendations on Reporting Electrode Potentials in Nonaqueous Solvents," International Union of Pure and Applied Chemistry—Divisional of Physical Chemistry—Commission on Electrochemistry, Pergamon Press Ltd, 1984.

European Office Action for EP Application No. 07723467.2 mailed Oct. 4, 2011.

Noviandri et al., 1999, "The Decamethylferrocenium/ Decamethylferrocene Redox Couple: A Superior Redox Standard to the Ferrocenium/Ferrocene Redox Couple for Studying Solvent Effects on the Thermodynamics of Electron Transfer," J. Phys. Chem. B, 1999, 103:6713-6722.

Translation of Japanese Office Action for JP Application No. 2009-500751 mailed Oct. 2, 2012.

Translation of Japanese Office Action for JP Application No. 2009-500772 mailed Oct. 2, 2012.

Yokoi et al., "Photochemical Doping of TCNQ by Photoinduced Electron Transfer and C-C Cleavage of Radical Cation," 1999, Chemistry Letters, pp. 241-242.

Korean Office Action mailed for KR Application No. 10-2008-7025710 on Aug. 26, 2013 (6 pages).

Korean Office Action mailed for KR Application No. 10-2008-7025710 on Feb. 27, 2014 (English translation) (4 pages).

\* cited by examiner

METHOD FOR PREPARING DOPED ORGANIC SEMICONDUCTOR MATERIALS AND FORMULATION UTILIZED THEREIN

CROSS-REFERENCE TO RELATED APPLICATION

This is a submission pursuant to 35 U.S.C. 154(d)(4) to enter the national stage under 35 U.S.C. 371 for PCT/EP2007/002510 filed Mar. 21, 2007. Priority is claimed under 35 U.S.C. 119(a) and 35 U.S.C. 365(b) to European Patent Application No. 06005687.6 filed Mar. 21, 2006 and European Patent Application No. 06005834.4 filed Mar. 22, 2006. The subject matters of PCT/EP2007/002510 and European Patent Application No. 06005687.6 and European Patent Application No. 06005834.4 are hereby expressly incorporated herein by reference.

The present invention relates to a method for preparing doped organic semiconductor materials as well as formulation which may be utilized in that method.

Organic semiconductors are constantly gaining ground in a multitude of applications, such as organic light emitting diodes (OLEDs), organic solar cells, organic thin film transistors (TFTs) radiofrequency identity tags (RFIDs), sensors and the like.

Organic materials are used in such applications, as they feature a superior processability to inorganic semiconductor materials. Organic materials can be easily evaporated in vacuum or processed from solution, whereas inorganic semiconductors like silicon or galliumarsenide are processed by PECVD, epitaxy processes or even in single crystal wafers. Especially the processing from solution promises to lead to significant cost savings, as simple processes like spin or dip coating, printing techniques or Langmuir-Blodgett techniques can be used to fabricate the layers. Further, organics offer not only simple processing methods but are also flexible in contrast to inorganic semiconductor materials that are brittle. However, inorganic semiconductors are far superior to organic materials in terms of conductivity and charge carrier mobility, which makes them still the number one choice for many applications.

One approach to improve the electrical properties of organic materials is the intentional redox doping of organic semiconductors. Here, small amounts of a strong donor (acceptor) material are added to the semiconductor host. Within the host material, the dopants undergo a chemical reaction with the matrix to release negative (positive) charges, i.e. an electron (a hole), to the transporting host material. This can be the case when dopant cations (anions) and host anions (cations) are formed. In the case of donor doped transport layers one refers to n-type doping, whereas acceptor doped layers are called p-type doped (both terms are used in analogy to inorganic semiconductor doping). A donor can be a compound with a low ionisation potential, an acceptor can be a compound with a high electron affinity.

By the use of these charge carrier dopants, the amount of free, persistent (steady-state) charge carriers within the transport material is increased, which directly translates in higher conductivities of the doped materials. The usefulness of doped transport layers is demonstrated for example in PIN OLEDs which use p- and n-doped charge carrier transport layers within the OLED architecture. By doing so, the operating voltage of the devices is reduced drastically due to reduced ohmic losses for the charge carrier transport through the doped layers and due to a reduction of the injection barrier from the electrons into the doped layers.

So far, the use of such a charge carrier transport doping of organic semiconductor materials is limited in many cases to layers which are produced via a thermal evaporation of matrix material and dopant. The reason for this is given by the fact that the chemical reaction of the donor or acceptor with the matrix changes the physical characteristics of the material drastically, for example Coulomb interaction of the matrix and the dopant sets in after the reaction. By the limitation to vacuum evaporation, one advantage of the organic semiconductor materials is lost, namely the easy processing from solution.

A direct processing of a mixture of the dopant and the matrix from solution is difficult due to the reaction that immediately sets in and leads to the formation of charge transfer complexes/organic salts. These have a completely different solubility than the original materials, which limits the processability of such a dopant-matrix solution drastically. Thus, separation of a doped phase and of an undoped phase can occur making it difficult to cast homogenous films. Solvents with high polarity (such as water) may be needed to dissolve the doped phase. Such solvents often pose difficulty for processing due to their limited electrochemical window, limited chemical stability, reactivity towards the dissolved material, incompatibility with previously prepared structures on the structure and unwanted effects of solvent traces in organic electronic devices. The shelf lifetime of such doped solutions can be short, too, because of unwanted side reactions of reactive species with the solvent.

It is one object of the present invention, to provide a method for preparing doped organic semiconductor materials, which overcomes the drawbacks of the prior art. Especially, the method shall be realizable in any easy and cost effective manner, in order to provide a homogeneous layer of dopant and organic material to be deposited onto a substrate.

This object is achieved by a method for preparing doped organic semiconductor materials comprising (i) preparing a solution or suspension containing at least one dopant precursor, at least one organic material to be doped and a solvent, (ii) applying the solution or suspension onto a substrate and removing the solvent, and (iii) converting the dopant precursor into a dopant by application of activation energy, wherein the dopant precursor is a dimer, oligomer, polymer, dispiro compound or polycycle of the dopant into which the dopant precursor is cleaved by application of activation energy. According to the invention is also the formulation containing at least one dopant precursor, at least one organic material to be doped and a solvent, wherein the dopant precursor is a dimer, oligomer, polymer, dispiro compound or polycycle of the dopant into which the dopant precursor is cleaved by application of activation energy, which can be utilized in the inventive methods.

Surprisingly, it was found that doping of organic semiconductor materials is easily possible from a solution, wherein a specific class of dopant precursors in solution which also contains an organic material to be doped, is provided. After application of the solution onto a substrate, preferably in the form of a film, the dopant precursors are activated to be cleaved into the actual dopants. This activation can be achieved by any of a number of energetic forms, which are suitable for this purpose and are apparent for someone skilled in the art.

In the present invention the term "dimer" is meant to comprise compounds which are generated by reaction of two monoradicals or diradicals with each other.

The term "oligomer" is meant to comprise compounds which are comprised of several diradicals, wherein a first radical terminus of the diradical reacts with a first of a further diradical, and a second terminus of the thus produced bigger diradical reacts with a second further diradical.

The term "polymer" is meant to comprise compounds which have compared to oligomers a higher number of diradicals incorporated.

A "dispiro compound" is according to the present invention an intramolecular addition product of a diradical, the radical centers of which are separated by a structural element of that kind, that said structural element connects the radical bearing carbon atoms, i.e. the carbon atoms which add to each other.

The term "polycycle" is meant to comprise an intramolecular addition product of a diradical, the radical centers of which are separated by a structural element of that kind that said structural element connects at least one other carbon atom than the ones bearing radicals (e.g. at least one atom in alpha position).

It is beneficial for the inventive method that preparation of the solution and application thereof onto a substrate as well as removal of a solvent are carried out in partial or complete preclusion of activation energy which is necessary for the conversion of the dopant precursor into a dopant, in order to prevent a premature cleavage of the dopant precursors. If necessary, further preparation steps may be carried out prior to the activation of the dopant precursor, which are known for someone skilled in the art.

After conversion of the dopant precursor into a dopant, the dopant will undergo a charge transfer with the matrix. In the case of n-type doping, the dopant will donate at least one eletron to the matrix. The matrix will be negatively charged, in consequence. Likewise the dopant will be singly (or multiply) positive charged. In the case of p-type doping, the dopant will accept an electron from the matrix. The matrix will be positively charged, in consequence. Likewise, the dopant will be singly (or multiply) negative charged.

In the following, the details of the doping are explained at the example of n-type doping. The mechanism for p-type doping is similar.

Upon activation of the dopant precursor it is subjected an irreversible cleavage of the binding so that the redox active species are released which react with the organic material to be doped, so that this material is doped. It is to be understood that doping of the organic material is on the basis of redox chemistry and not on the basis of acid/base chemistry. In order to avoid acid/base chemistry it is especially preferred that upon cleavage no hydrogen or (Lewis) acid is released. It is known that protons or acids can lead to a p-doping effect in organic materials. The release of hydrogen or acid therefore may lead to an unwanted compensation of the n-doping effect. The irreversible cleavage of the binding is believed to be due to an excitation of the dopant precursor or the matrix followed by an electron transfer from the dopant precursor to the matrix. The dopant precursor is thus oxidized. It is believed that the dopant precursor is subject to irreversible bond cleavage in the oxidized state. Radicalic dopants and/or the dopant cations are formed. The irreversible nature of the bond cleavage prevents the back-transfer of the electron and stabilizes the doped state.

If dopant precursors for p-type doping are employed, it is especially preferred that upon cleavage no (Lewis) base is released. It is known that bases can lead to a n-type doping effect in organic materials. This may lead to an unwanted compensation of the intended p-doping effect.

In a preferred embodiment of the present invention the dopant precursor for n-type doping solely consists of donor like moieties, which are released during cleavage of the dopant precursor. In an especially preferred embodiment the donor like moieties are identical. For p-type doping, it is preferred that the dopant precursor solely consists of acceptor like moieties, which are released during activation.

It is preferred that the solvent of the solution is of low polarity. It can be selected for instance from toluol, tetrahydrofuran or methylene chloride. The low polarity of the solvent stabilizes the unreacted state of dopant precursor and matrix in the solution.

In a preferred embodiment of the present invention the solution is kept in the dark and/or cooled during the storage and processing the layer.

The invention allows processing from a solution, as no salts are formed in the solution, as long as no suitable activation energy for cleavage is applied. Utilizing this method it is possible to prepare a layer from the solution prepared, for example by standard coating or printing techniques.

One requirement for doped organic materials, for example in OLEDs, is that the excitons created within the emission zone have energies high enough to create visible light. The highest energy is needed for an emission in the blue range of the spectrum with a wavelength of 400-475 nm. To avoid additional injection barriers within the OLED device, it is desirable to choose the energy levels of hole transport layer and electron transport layer carefully, such that the energy levels match with the emission zone.

In this respect, reduction potential of materials can be provided as voltage value vs. $Fc/Fc^+$. $Fc/Fc^+$ denotes the ferrocen/ferrocenium reference couple. Reduction potentials can be measured for instance by cyclic voltammetry in a suitable solvent for instance acetonitrile or tetrahydrofuran. Details of cyclovoltammetry and other methods to determine reduction potentials and the relation of the ferrocen/ferrocenium reference couple to various reference electrodes can be found in A. J. Bard et al., "Electrochemical Methods: Fundamentals and Applications", Wiley, 2. Edition, 2000.

An alternative measure for the oxidation strength of the donor dopant molecule can be ultraviolet photoelectron spectroscopy (UPS). By this method, the ionisation potential is determined. It has to be distinguished, whether the experiment is carried out in the gas phase or in the solid phase, i.e. by investigation of a thin film of the material. In the latter case, solid state effects such as the polarisation energy of the hole remaining in the solid after removal of a photoelectron give rise to deviations in the ionisation potential as compared to gas phase values. A typical value for the polarisation energy is around 1 eV (E. V. Tsiper et al., Phys. Rev. B 195124/1-12 (2001)).

For typical electron transport materials in OLED, the reduction potential is around −2.3 V vs. $Fc/Fc^+$. For typical electron transport materials in solar cells, the reduction potential is around −1 V vs. $Fc/Fc^+$. For a typical hole transport material in OLED, the oxidation potential is around 0.2 V vs. $Fc/Fc^+$.

An oxidation potential of the n-type dopant is equal or lower than about −1 V vs. $Fc/Fc^+$, preferably equal or lower than −2.0 V vs. $Fc/Fc^+$, more preferably equal or lower than −2.2 V vs. $Fc/Fc^+$.

An reduction potential for the p-type dopant is equal or higher than 0 V vs. $Fc/Fc^+$.

It is preferred for the present invention that matrix and dopant precursor do not spontaneously react in the solution, but only after proper activation. It is believed that a spontaneous electron transfer from the dopant precursor and the matrix can occur if the oxidation potential of the former $V_{ox\_DP}$ and the reduction potential of the latter $V_{red\_Mat}$ are close. As an example, 10c,10c'-bi(8,9-dimethyl-2,3,5,6-tetrahydro-1H,4H-3a,6a,10b-triaza-fluoranthenyl) (Dimer) is reacting spontaneously with naphthalene tetracarboxylic dianhydrid (NTCDA) at room temperature even in the absence of light. The oxidation potential of 10c,10c'-Bi(8,9-dimethyl-2,3,5,6-tetrahydro-1H,4H-3a,6a,10b-triaza-fluoranthenyl) is −0.74 V vs. Fc/Fc+ (in tetrahydrofuran), and the reduction potential of NTCDA is about −0.79 V vs. Fc/Fc+ (in dichlormethane). It is thus preferable that $V_{ox\_DP}$-$V_{red\_Mat}$ is at least greater than 0.05 V, preferably greater than 0.2 V, more preferably greater than 1 V. A greater difference reduces the speed of thermal electron transfer by increasing the energy barrier for the process. The solution becomes easier to handle at room temperature, and will be activated only be irradiation with light. It is beneficial that the corresponding energy levels are chosen such that the activation is possible only be highly energetic (e.g. blue) light, but not by lowly energetic light (e.g. yellow). This facilitates the handling in typical production facilities where yellow-light conditions are observed. The processes can be supervised visually by the operator but premature activation is prevented.

Further it is beneficial that the dopant precursor in the course of the cleavage releases only components of a certain minimum size. In this case the diffusion of the dopants within the layer or towards adjacent layers is hindered or even prevented. It is therefore preferred that the dopant consists of at least 2, more preferred at least 3 or more cycles. These cycles can be bonded or fused to each other and may be saturated or unsaturated. They may or may not contain heteroatoms. Further it is preferred that the dopant consists of at least 15 atoms, more preferred of at least 35 atoms. The molar mass of the dopant is preferred to be greater than 100 g/mol, more preferred greater than 200 g/mol. It is to be understood, that for the dopant precursor, accordingly, at least twice these weight or size values apply.

Suitable matrix materials to form a doped layer according to the present invention could be small-molecule electron transport materials such as from quinolinato complexes of main group metals, phthalocyanine complexes, porphyrine complexes, phenanthrolines, oxadiazoles, heteroaromatics, especially N-heteroaromatics, and mixtures thereof. Especially suitable are conjugated polymers or oligomers as depicted below, where x and y vary between 0 to 5, and where either of the numbers is different from 0.

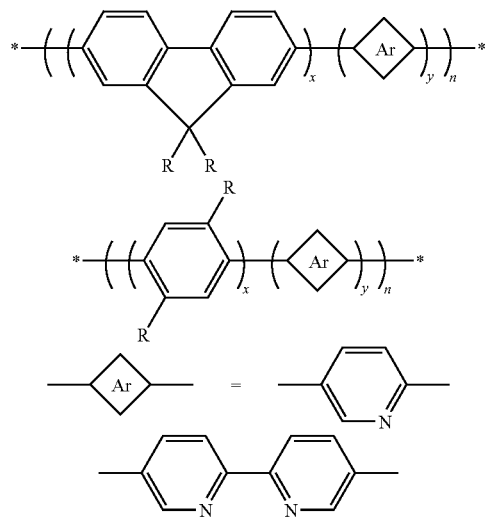

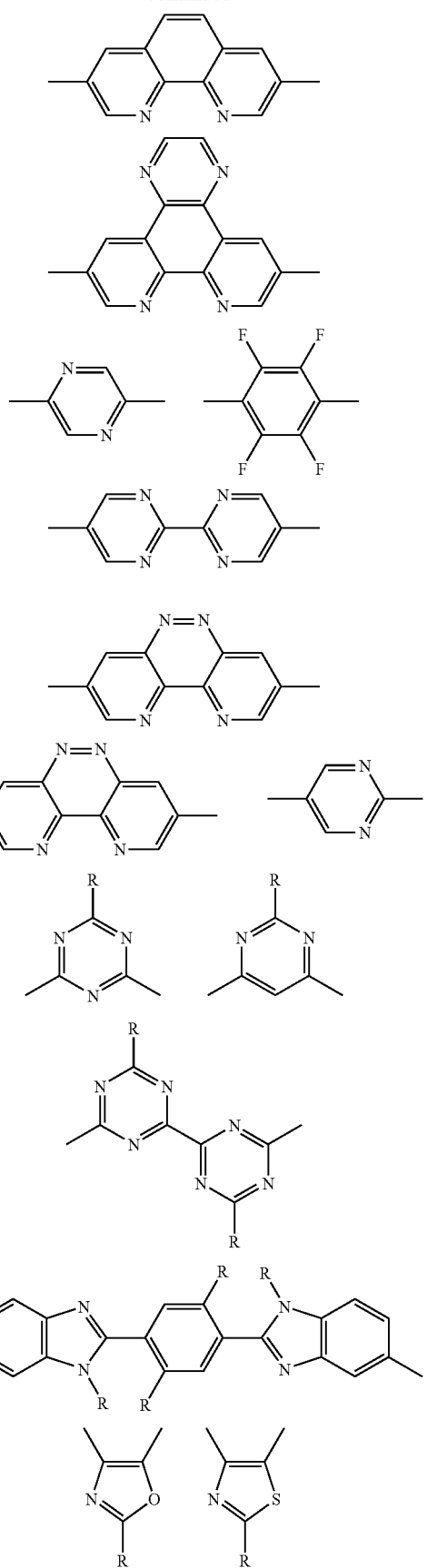

-continued

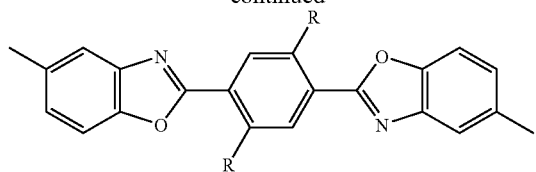
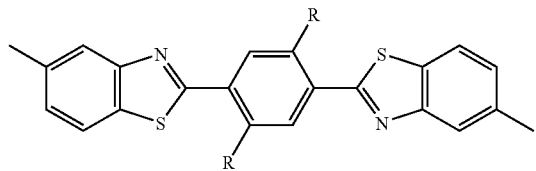
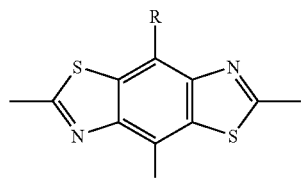
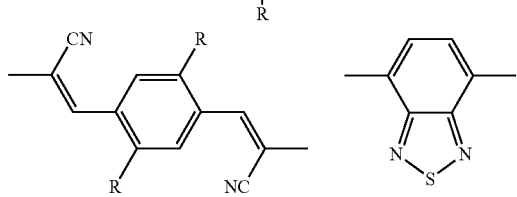
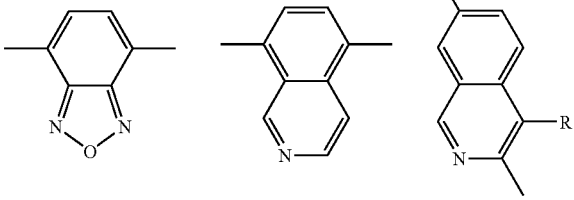
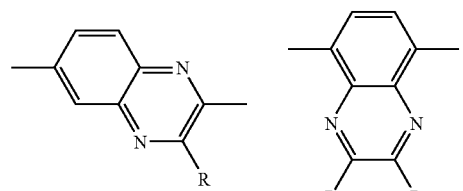
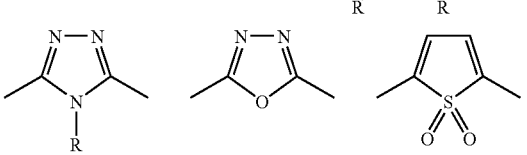
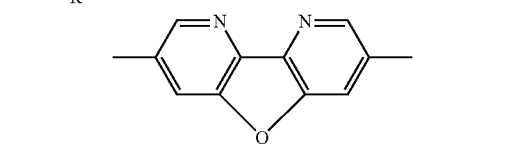
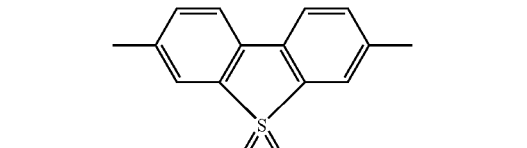
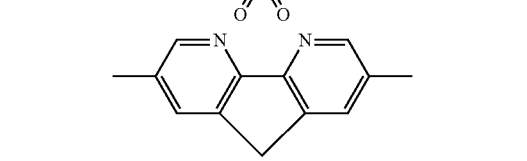

-continued

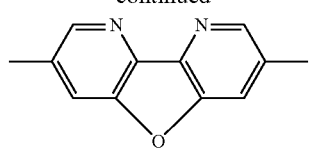
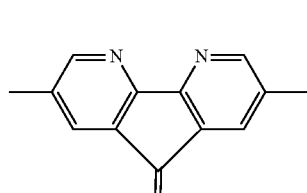
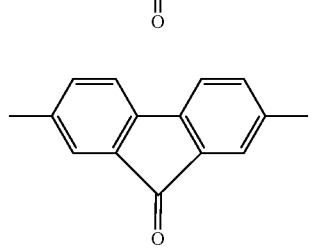

R = Alkyl-, -OAlkyl, Perfluoroalkyl, any substituted Alkyl-, Aryl-, Perfluoroaryl-, any substituted Aryl-,
—(O—CH$_2$CH$_2$)$_n$—OCH$_3$ Further suitable matrix materials are side-chain polymers, as depicted below.

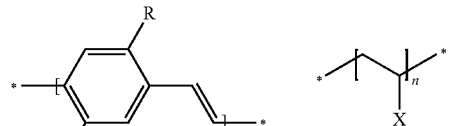
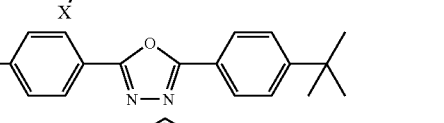
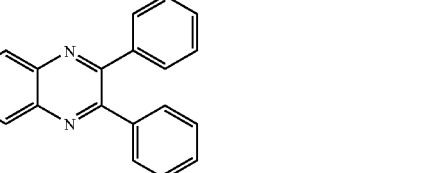

R = Alkly-, OAlkyl, Perfluoroalkyl, any substituted Alkyl-, Aryl-, Perfluoroaryl-, any substituted Aryl-, —(O—CH$_2$CH$_2$)$_n$—OCH$_3$ Especially useful is the [6,6]-phenyl C-61-butyric acid methyl ester (PCBM) as a matrix material. It is frequently used in organic solar cells as electron transporting component.

Particularly preferred are the following dopants

1a

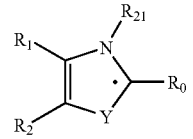

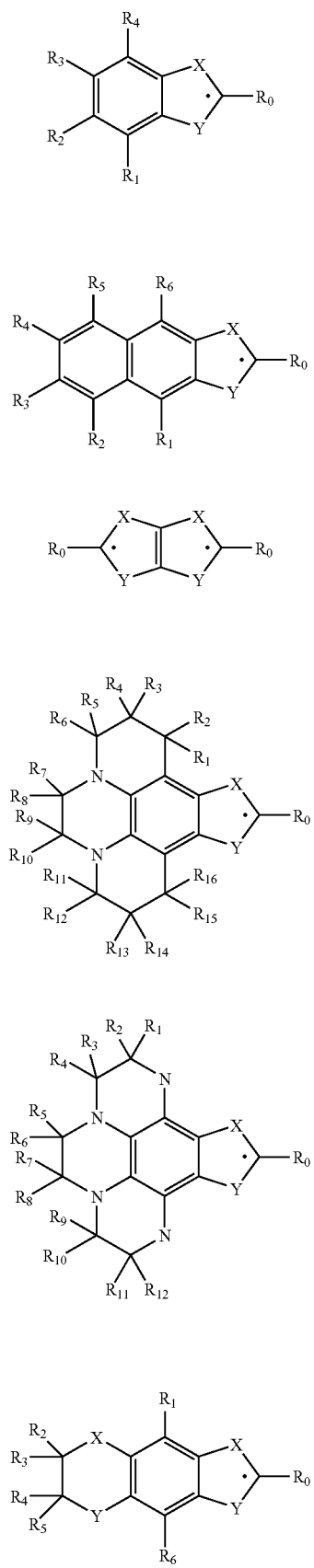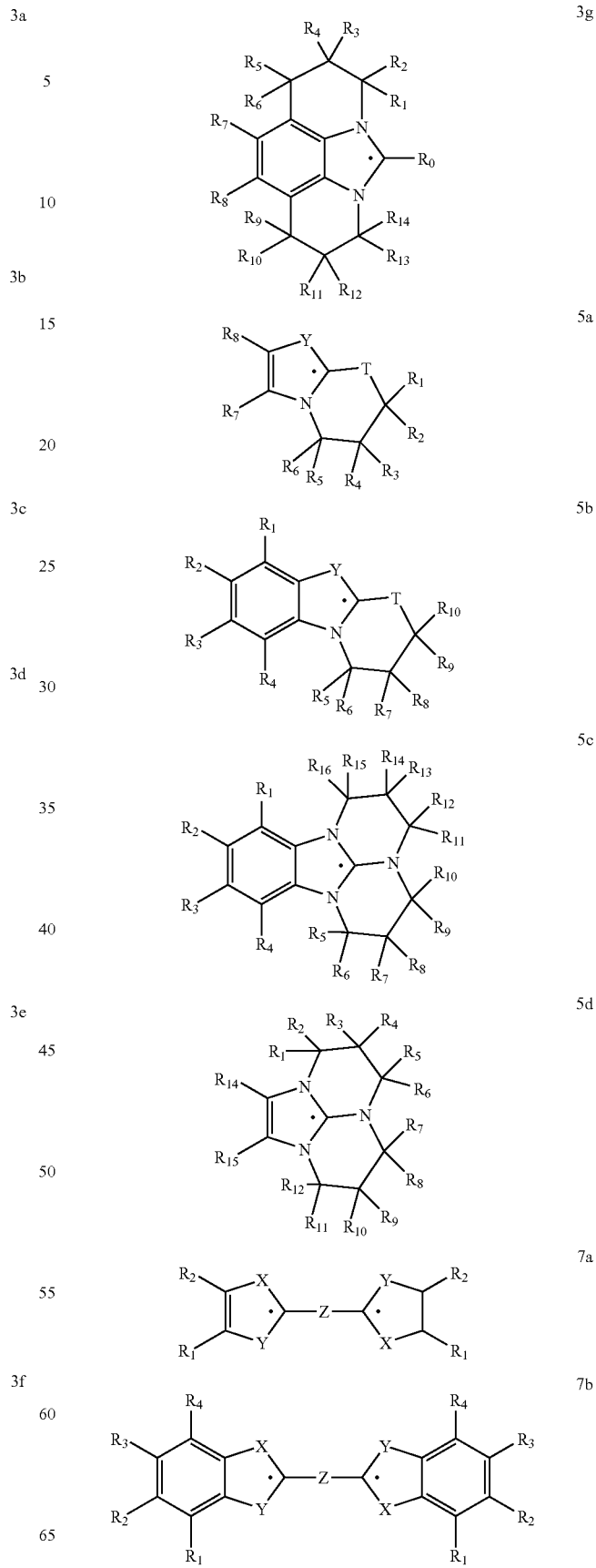

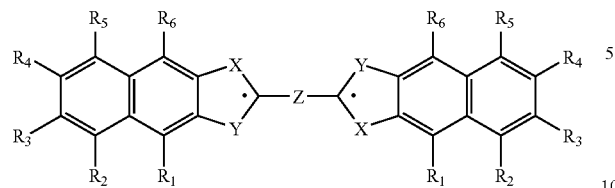

7c

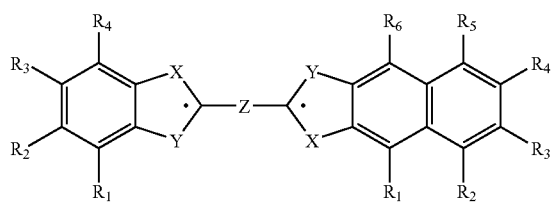

7d

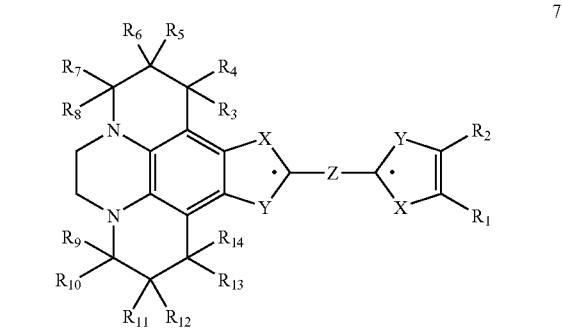

7e

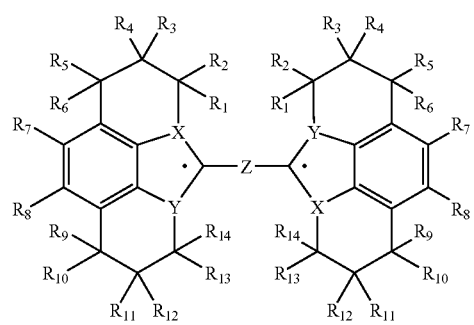

7f

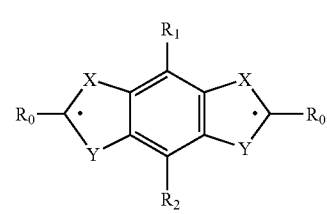

7g

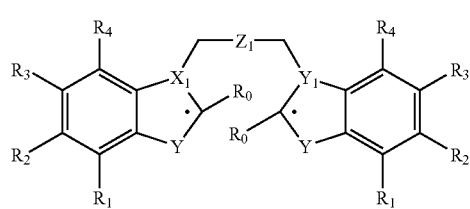

7h

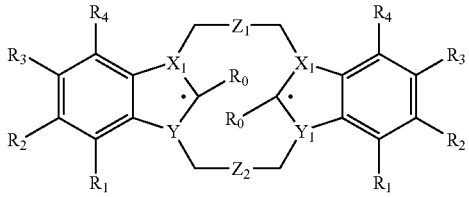

7i

Where $X_1$, $Y_1$ is N or P, with $R_0$, $R_1$-$R_{16}$ as defined for the R's in claim 2.

Additional features and advantages of the present invention are further illustrated in the following examples which are not to be considered to restrict the scope of the invention in any way.

For preparing a film from solution, the spin-on-technique has been used (substrate at room temperature, 3000 revolutions per minute), unless otherwise specified. All handling of the solutions has been carried out in a glove box. The preparation of films and the handling has been carried out in a glove box. For some experiments, the film has been transferred in a high vacuum chamber. Films have been deposited onto glass substrates equipped with parallel ITO contacts having a length of 14 mm and separation of 1.25 mm. Current measurement has been carried out by applying a voltage of 10 V on the parallel ITO contacts. From current, voltage and geometry of the samples, the conductivity has been calculated.

EXAMPLE 1a (COMPARATIVE)

A solution of 105 mg of poly[9,9-dioctylfluorenyl-2,7-diyl)-co-1,4-benzo-{2,1'-3}thiadiazole)(YE) has been dissolved in 7 ml of toluol.

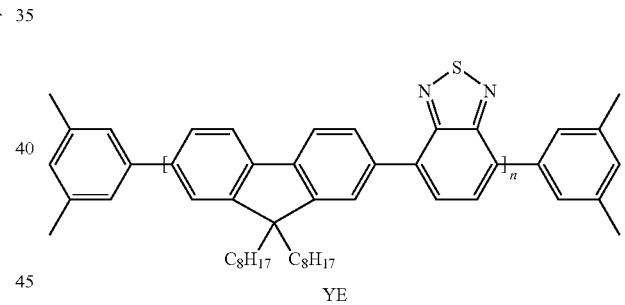

YE

A thin film of YE has been prepared from the solution. The film did not show any current ($<10^{-11}$ A). The layer thickness was estimated as 50 mn by optical methods.

In a second step, the film has been introduced into a high vacuum. 5 nm of Tetrakis(1,2,3,3a,4,5,6,6a,7,8-decahydro-1,9,9b-triazaphenalenyl)ditungsten(II) (Ndop) have been evaporated onto the film. After deposition, the current was increased by two order of magnitude to a current of $10^{-9}$ A. This demonstrates that Ndop has in principle sufficient dopant strength in order to induce conductivity in YE.

EXAMPLE 1b (COMPARATIVE)

A solution of 105 mg of of poly[9,9-dioctylfluorenyl-2,7-diyl)-co-1,4-benzo-{2,1'-3}thiadiazole)(YE) has been dissolved in 7 ml of toluol. To prepare a mixture of YE and Ndop, 3 mg of Ndop has been added to 2 ml of said solution.

A thin film has been casted by spin-on technique from the mixture. A current below the measurement limit of $10^{-11}$ A has been observed. In the light of example 1a (comparative), one can conclude that YE can not be doped by Ndop by solution processing even though the doping strength of Ndop is sufficient.

Drops of the solution have been allowed to dry on another substrate. It has been found that the resulting film is inhomogeneous. It showed a very small current of 190 pA.

In summary, the comparative example demonstrates the difficulties encountered in the processing of solutions containing matrix and donor moieties.

EXAMPLE 2 (INVENTIVE)

A solution of 10 mg of poly[9,9-dioctylfluorenyl-2,7-diyl)-co-1,4-benzo-{2,1'-3}thiadiazole)(YE) has been dissolved in 1 ml of toluol. A solution of 10c,10c'-Bi(8,9-dimethyl-2,3,5,6-tetrahydro-1H,4H-3a,6a,10b-triazafluoranthenyl) (Dimer) has been prepared by dissolving 10 mg of Dimer in 1 ml of Toluol. A mixed solution of YE:Dimer has been prepared by mixing 1 ml YE-solution and 100 µl of Dimer-solution.

A thin film has been casted by spin-on from the mixture. A current of 180 pA was measured. The thickness of the layer was estimated as about 50 nm by optical methods. The corresponding conductivity of the layer was about $3*10^{-7}$ S/cm.

A drop of the mixed solution has been allowed to dry on another substrate. It has been found that the resulting film is homogeneous. Initially, it was transparent yellow. After exposure to ambient light for a week it exhibited a dark brown colour. This indicates that a chemical reaction has occurred. After exposure it showed a current of 180 nA.

EXAMPLE 3 (INVENTIVE)

A solution of 105 mg of poly[9,9-dioctylfluorenyl-2,7-diyl)-co-1,4-benzo-{2,1'-3}thiadiazole)(YE) has been dissolved in 7 ml of toluol. A solution of 10c,10c'-Bi(8,9-dimethyl-2,3,5,6-tetrahydro-1H,4H-3a,6a,10b-triazafluoranthenyl) (Dimer) has been prepared by dissolving 15 mg of Dimer in 1 ml of Toluol. A mixed solution of YE:Dimer has been prepared by mixing 1 ml YE-solution and 100 µl of Dimer-solution. The film has been prepared by spin-on from the mixed solution. All steps have been carried out under restricted light conditions.

It is a property of a restricted light condition that blue and green light is prevented from reaching the solvent and the sample during preparation and handling. This is achieved by covering the handling area with orange coloured transparent foils having the colour RAL 1028. The sample has been introduced into a vacuum chamber. In the absence of green or blue light, no conductivity is detected for the sample. Finally, white light has been directed onto the sample. A current of 2.1 nA has been detected, corresponding to a conductivity of $4*10^{-6}$ S/cm (estimated layer thickness is 50 nm). This example demonstrates that the difficulties encountered with ionic solution in the processing of thin films can be avoided by using the inventive dopants. The reduction potential of YE is −1.92 V vs. Fc/Fc$^+$ in DCM. Thus, the energetic difference of the oxidation potential of dimer and the reduction potential of YE is larger than 1 eV. This ensures that in the absence of light of sufficient energy, no activation of the dopant precursor takes place.

EXAMPLE 4 (INVENTIVE)

The film has been prepared with the same conditions as disclosed for example 3. After preparation, the film has been exposed to ambient air in the absence of light for 10 minutes. Afterwards, the sample has been introduced into a vacuum chamber and exposed with white light. A current of 1.4 nA is measured after exposure.

The example demonstrates that in the absence of light the film can be exposed even to oxygen and/or moisture without negative effect for the resulting conductivity after exposure with light. It is well known that the conductivity of conventional n-doped films is quickly lost due to high reactivity of the ionic species towards oxygen. This allows, for instance, to produce an OLED including the n-doped electron transport layer, by solution processing in air. This can facilitate production, where providing inert atmosphere during printing on large substrates is an issue. The process may involve printing the electron transport layer in ambient air, preferably in the absence of light. In a later step, the organic layers may be introduced into a vacuum in order to remove trace amounts oxygen and water from the organic layers, followed by activation of the dopant precursor.

The features disclosed in foregoing description and in the claims may, both separately and in any combination thereof, be material for realizing the invention in diverse forms thereof.

The invention claimed is:

1. A method for preparing doped organic semiconductor materials comprising the following steps:

(i) preparing a solution or suspension comprising at least one dopant precursor, at least one organic material to be doped, and a solvent, (ii) applying the solution or suspension onto a substrate and removing the solvent, and (iii) converting the dopant precursor into a dopant by application of activation energy, wherein the dopant precursor is a dimer, oligomer, polymer, dispiro compound, or polycycle of the dopant into which the dopant precursor is cleaved by application of activation energy, wherein the difference between the oxidation potential of the dopant precursor and reduction potential of the organic material to be doped is greater than 0.05 V, and wherein the dopant is selected from the group consisting of:

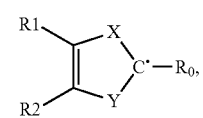

1

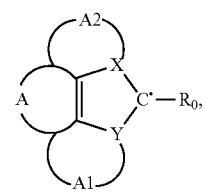

3

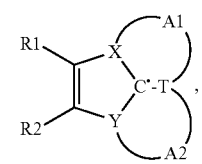

5

-continued

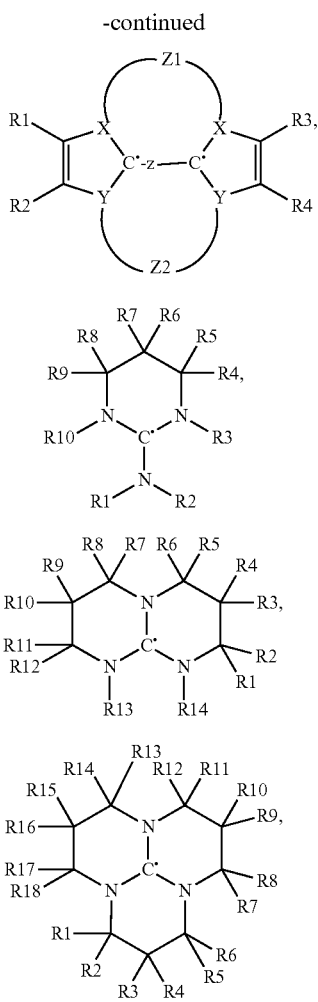

wherein structure 3 comprises one or more cyclic linkages selected from the group consisting of A, $A_1$, and $A_2$, wherein A, $A_1$, and $A_2$, independent of each other, comprise, substituted or unsubstituted, carbocyclic, heterocyclic, or polycyclic ring systems;

wherein in structure 5 $A_1$ and $A_2$ are present alone or together and are as defined above, wherein T is selected from the group consisting of $CR_{22}$, $CR_{22}R_{23}$, N, $NR_{21}$, O, and S;

wherein structure 7 comprises one or more bridging linkages selected from the group consisting of Z, $Z_1$, and $Z_2$, and wherein Z, $Z_1$, and $Z_2$ are independently selected from alkyl, alkenyl, alkynyl, cycloalkyl, sililyl, alkylsililyl, diazo, disulfide, heterocycloalkyl, heterocyclyl, piperazinyl, dialkylether, polyether, primary alkyl amine, arylamine and polyamine, aryl, or and heteroaryl;

wherein in structures 8a-8c the ring per heterocycle comprises from 5 to 7 atoms, wherein X and Y are independently selected from the group consisting of O, S, N, $NR_{21}$, P, and $PR_{21}$; and $R_{0-18}$, $R_{21}$, $R_{22}$, and $R_{23}$ are independently selected from, substituted or unsubstituted, aryl, heteroaryl, heterocyclyl, diarylamine, diheteroarylamine, dialkyl amine, heteroarylalkylamine, arylalkylamine, H, F, cycloalkyl, halogencycloalkyl, heterocycloalkyl, alkyl, alkenyl, alkynyl, trialkylsilyl, triarylsilyl, halogen, styryl, alkoxy, aryloxy, thioalkoxy, thioaryloxy, sililyl, trialkylsilylalkynyl, or a (hetero)aliphatic or y, (hetero)aromatic ring system, wherein the (hetero)aliphatic or (hetero)aromatic ring system comprises one or more of $R_{0-18}$, $R_{21}$, $R_{22}$, and $R_{23}$, the organic material to be doped has a reduction potential vs. $Fc/Fc^+$ that is more negative than $-1.0$ V, and wherein no hydrogen or Lewis acid is released upon cleavage.

2. The method according to claim 1, wherein the activation energy in step (iii) comprises photoenergy, microwaves, ultrasound, thermal energy, electrical energy, or a combination thereof.

3. The method according to claim 1, wherein the organic material to be doped and the dopant precursor are in non-charged condition.

4. The method according to claim 1, wherein step (ii) further comprises forming a film on the substrate.

5. The method according to claim 4, wherein the film is prepared by spin-coating, dip-coating, or printing techniques.

6. The method according to claim 1, wherein in step (iii) the dopant precursor is irreversibly cleaved.

7. The method according to claim 1, wherein the dopant precursor consists of donor like moieties, which are cleaved during application of energy.

8. The method according to claim 1, wherein the dopant precursor is selected so that a n-dopant generated therefrom has an oxidation potential of equal or lower than $-1.5$ V vs. $Fc/Fc^+$.

9. The method according to claim 1, wherein the solvent is selected from tetrachloromethane, benzene, methylene chloride, chloroform, or tetrahydrofuran.

10. The method according to claim 1, wherein the organic material to be doped is selected from quinolinato complexes of main group metals, phthalocyanine complexes, porphyrine complexes, phenanthrolines, oxadiazoles, heteroaromatics, or mixtures thereof.

11. The method according to claim 1, characterized in that the organic material to be doped is selected from: conjugated polymers, co-polymers or oligomers, or side-chain polymers with charge transporting function.

12. The method according to claim 1, wherein the substrate is selected from flexible substrate, glass substrate, metal substrate, polymer film, or inorganic semiconductor.

13. A method for preparing doped organic semiconductor materials comprising the following steps:

(i) preparing a solution or suspension comprising at least one dopant precursor, at least one organic material to be doped, and a solvent, (ii) applying the solution or suspension onto a substrate and removing the solvent, and (iii) converting the dopant precursor into a dopant by application of activation energy, wherein the dopant precursor is a dimer, oligomer, polymer, dispiro compound, or polycycle of the dopant into which the dopant precursor is cleaved by application of activation energy wherein steps (i) and (ii) are carried out under partial or complete preclusion of activation energy which is required for the conversion of the dopant precursor into a dopant, and wherein the dopant is selected from the group consisting of:

1

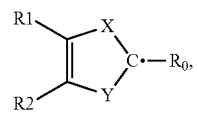

3

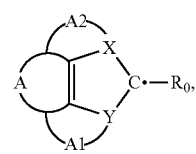

5

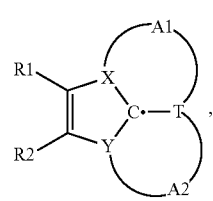

7

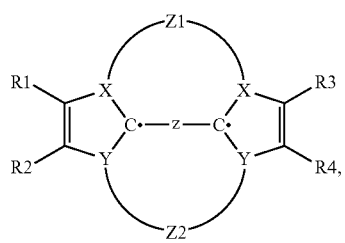

8a

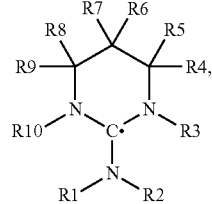

8b

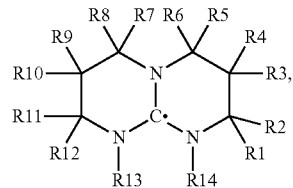

-continued

8c

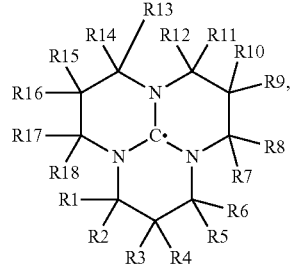

wherein structure 3 comprises one or more cyclic linkages selected from the group consisting of A, $A_1$, and $A_2$, wherein A, $A_1$, and $A_2$, independent of each other, comprise, substituted or unsubstituted, carbocyclic, heterocyclic, or polycyclic ring systems;

wherein in structure 5 $A_1$ and $A_2$ are present alone or together and are as defined above, wherein T is selected from the group consisting of $CR_{22}$, $CR_{22}R_{23}$, N, $NR_{21}$, O, and S;

wherein structure 7 comprises one or more bridging linkages selected from the group consisting of Z, $Z_1$, and $Z_2$, and wherein Z, $Z_1$, and $Z_2$ are independently selected from alkyl, alkenyl, alkynyl, cycloalkyl, sililyl, alkylsililyl, diazo, disulfide, heterocycloalkyl, heterocyclyl, piperazinyl, dialkylether, polyether, primary alkyl amine, arylamine and polyamine, aryl, or and heteroaryl;

wherein in structures 8a-8c the ring per heterocycle comprises from 5 to 7 atoms, wherein X and Y are independently selected from the group consisting of O, S, N, $NR_{21}$, P, and $PR_{21}$;and $R_{0-18}$, $R_{21}$, $R_{22}$, and $R_{23}$ are independently selected from, substituted or unsubstituted, aryl, heteroaryl, heterocyclyl, diarylamine, diheteroarylamine, dialkyl amine, heteroarylalkylamine, arylalkylamine, H, F, cycloalkyl, halogencycloalkyl, heterocycloalkyl, alkyl, alkenyl, alkynyl, trialkylsilyl, triarylsilyl, halogen, styryl, alkoxy, aryloxy, thioalkoxy, thioaryloxy, sililyl, trialkylsilylalkynyl, or a (hetero)aliphatic or (hetero)aromatic ring system, wherein the (hetero)aliphatic or (hetero) aromatic ring system comprises one or more of $R_{0-18}$, $R_{21}$, $R_{22}$, and $R_{23}$, the organic material to be doped has a reduction potential vs. $Fc/Fc^+$ that is more negative than +1.0 V, and wherein no hydrogen or Lewis acid is released upon cleavage.

* * * * *

UNITED STATES PATENT AND TRADEMARK OFFICE
CERTIFICATE OF CORRECTION

PATENT NO. : 9,065,055 B2  Page 1 of 1
APPLICATION NO. : 12/293765
DATED : June 23, 2015
INVENTOR(S) : Olaf Zeika et al.

It is certified that error appears in the above-identified patent and that said Letters Patent is hereby corrected as shown below:

On the Title page, Item (75) Inventors: after "Martin Ammann, Dresden (DE)" insert --Sven Zimmermann, Dresden (DE)--

Signed and Sealed this
Twenty-second Day of March, 2016

Michelle K. Lee
*Director of the United States Patent and Trademark Office*